(12) United States Patent
Hsieh et al.

(10) Patent No.: US 11,433,225 B2
(45) Date of Patent: Sep. 6, 2022

(54) MICRONEEDLE STRUCTURE AND BIODEGRADABLE MICRONEEDLE THEREOF

(71) Applicant: MICROBASE TECHNOLOGY CORP., Taoyuan (TW)

(72) Inventors: Shu-Pin Hsieh, Taoyuan (TW); Ting-Kai Tsai, Taoyuan (TW)

(73) Assignee: MICROBASE TECHNOLOGY CORP., Taoyuan (TW)

( * ) Notice: Subject to any disclaimer, the term of this patent is extended or adjusted under 35 U.S.C. 154(b) by 224 days.

(21) Appl. No.: 16/862,699

(22) Filed: Apr. 30, 2020

(65) Prior Publication Data

US 2020/0360678 A1 Nov. 19, 2020

(30) Foreign Application Priority Data

May 15, 2019 (TW) ................................ 108116699

(51) Int. Cl.
*A61M 37/00* (2006.01)

(52) U.S. Cl.
CPC . *A61M 37/0015* (2013.01); *A61M 2037/0046* (2013.01)

(58) Field of Classification Search
CPC ...... A61M 37/0015; A61M 2037/0046; A61M 2037/0053
See application file for complete search history.

(56) References Cited

U.S. PATENT DOCUMENTS

| 2003/0135161 | A1* | 7/2003 | Fleming | A61B 5/14514 606/186 |
| 2008/0200883 | A1* | 8/2008 | Tomono | A61M 37/0015 604/272 |
| 2011/0237925 | A1* | 9/2011 | Yue | A61K 9/0021 156/278 |
| 2014/0180201 | A1* | 6/2014 | Ding | A61M 37/0015 264/255 |
| 2014/0243867 | A1* | 8/2014 | Lim | A61B 5/15134 264/250 |

(Continued)

FOREIGN PATENT DOCUMENTS

| CN | 104815398 A | 8/2015 |
| CN | 205360022 U | 7/2016 |

(Continued)

*Primary Examiner* — Amber R Stiles
(74) *Attorney, Agent, or Firm* — Li & Cai Intellectual Property (USA) Office

(57) ABSTRACT

A microneedle structure and a biodegradable microneedle thereof are provided. The biodegradable microneedle defining a central axis includes a first step portion and a second step portion that is taperedly extending from the first step portion along the central axis. The biodegradable microneedle has a total height along the central axis and a maximum internal diameter along a direction perpendicular to the central axis. The total height is within a range of 380-430 μm, and an aspect ratio defined by the total height divided by the maximum internal diameter is within a range of 1.2-2.2. In a cross section of the biodegradable microneedle having the central axis, a part of the second step portion arranged away from the first step portion having a corner. The corner has an angle within a range of 65-100 degrees and faces toward the first step portion.

10 Claims, 7 Drawing Sheets

(56) References Cited

U.S. PATENT DOCUMENTS

| | | | |
|---|---|---|---|
| 2015/0094648 A1 | 4/2015 | Toyohara et al. | |
| 2015/0238743 A1* | 8/2015 | Che | B29C 33/40 |
| | | | 156/285 |
| 2017/0036003 A1 | 2/2017 | Wakamatsu et al. | |
| 2017/0258712 A1* | 9/2017 | Oomori | B29C 67/243 |
| 2019/0001109 A1* | 1/2019 | Kim | A61K 47/36 |

FOREIGN PATENT DOCUMENTS

| | | |
|---|---|---|
| CN | 108939282 A | 12/2018 |
| CN | 109152914 A | 1/2019 |
| CN | 210020851 U | 2/2020 |
| TW | 458791 B | 10/2001 |
| WO | 2016149152 A1 | 9/2016 |
| WO | WO 2017116076 A1 | 7/2017 |

\* cited by examiner

MICRONEEDLE STRUCTURE AND BIODEGRADABLE MICRONEEDLE THEREOF

CROSS-REFERENCE TO RELATED PATENT APPLICATION

This application claims the benefit of priority to Taiwan Patent Application No. 108116699, filed on May 15, 2019. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a microneedle, and more particularly to a microneedle structure and a biodegradable microneedle thereof.

BACKGROUND OF THE DISCLOSURE

For a conventional microneedle structure applied to human skin, microneedles of the conventional microneedle structure are limited to certain shapes, so that the conventional microneedle does not have enough structural strength. In order to prevent the conventional microneedle from being deformed due to without having enough structural strength, the conventional microneedle is always formed with other structural limitations. For example, a tip of the conventional microneedle has an angle within a range of 15-60 degrees for preventing the conventional microneedle from being deformed when contacting human skin.

SUMMARY OF THE DISCLOSURE

In response to the above-referenced technical inadequacies, the present disclosure provides a microneedle structure and a biodegradable microneedle thereof to effectively improve on the issues associated with conventional microneedles.

In one aspect, the present disclosure provides a microneedle structure, which includes a base and a plurality of biodegradable microneedles disposed on the base and each defining a central axis. Each of the biodegradable microneedles has a total height along the central axis and a maximum internal diameter along a direction perpendicular to the central axis. The total height is within a range of 380-430 μm, and an aspect ratio defined by the total height divided by the maximum internal diameter is within a range of 1.2-2.2. Each of the biodegradable microneedles includes a first step portion connected to the base and a second step portion taperedly extending from the first step portion along a direction away from the base. In a cross section of each of the biodegradable microneedles having the central axis, a part of the second step portion arranged away from the first step portion has a corner. The corner has an angle within a range of 65-100 degrees and faces toward the first step portion.

In certain embodiments, in each of the biodegradable microneedles, the second step portion includes a contacting end arranged away from the first step portion, and the contacting end has an arced surface having a diameter within a range of 10-25 μm.

In certain embodiments, in each of the biodegradable microneedles, the first step portion is tapered along a direction away from the base, and a top surface of the first step portion is entirely overlapped with a bottom surface of the second step portion.

In certain embodiments, the base is biodegradable, and the base and the biodegradable microneedles are integrally formed as a one piece structure.

In certain embodiments, the total height of each of the biodegradable microneedles is within a range of 380-400 μm.

In certain embodiments, in each of the biodegradable microneedles, the first step portion is a pyramidal frustum, the second step portion is a pyramid, a bottom surface of the first step portion is connected to the base, and a top surface of the first step portion is entirely overlapped with a bottom surface of the second step portion.

In certain embodiments, a ratio defined by a height of the first step portion in the total height divided by a height of the second step portion in the total height is within a range of 6.2-7.0.

In certain embodiments, in each of the biodegradable microneedles, the first step portion is a conical frustum, the second step portion is a cone, a bottom surface of the first step portion is connected to the base, and a top surface of the first step portion is entirely overlapped with a bottom surface of the second step portion.

In certain embodiments, a ratio defined by a height of the first step portion in the total height divided by a height of the second step portion in the total height is within a range of 1.8-2.6.

In one aspect, the present disclosure provides a biodegradable microneedle of a microneedle structure defining a central axis. The biodegradable microneedle includes a first step portion and a second step portion that is taperedly extending from the first step portion along the central axis. The biodegradable microneedle has a total height along the central axis and a maximum internal diameter along a direction perpendicular to the central axis, wherein the total height is within a range of 380-430 μm, and an aspect ratio defined by the total height divided by the maximum internal diameter is within a range of 1.2-2.2. In a cross section of the biodegradable microneedle having the central axis, a part of the second step portion arranged away from the first step portion has a corner. The corner has an angle within a range of 65-100 degrees and faces toward the first step portion.

Therefore, the biodegradable microneedle of the microneedle structure in the present disclosure is a two-step structure different from structure of conventional microneedle, thereby effectively reinforcing the structural strength of the biodegradable microneedle. Specifically, the biodegradable microneedle can have a stronger structural strength based on the design of the two-step structure (e.g., the aspect ratio), so that the angle of the corner of the second step portion is not limited to the conventional limitations for being manufactured easily and being applied broader.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

Figure 1:
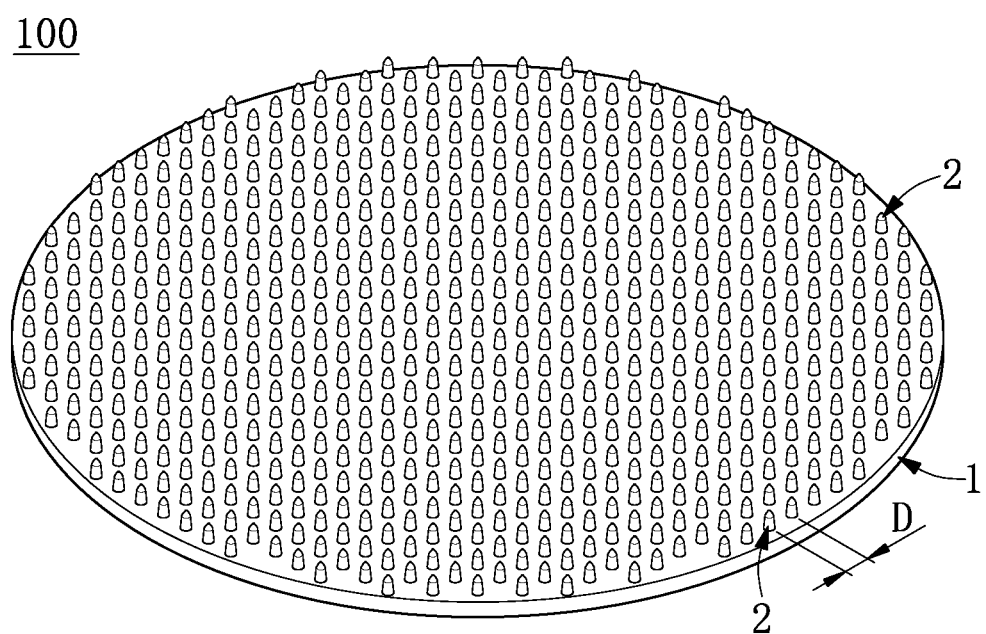
FIG. 1 is a perspective view of a microneedle structure according to a first embodiment of the present disclosure.

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
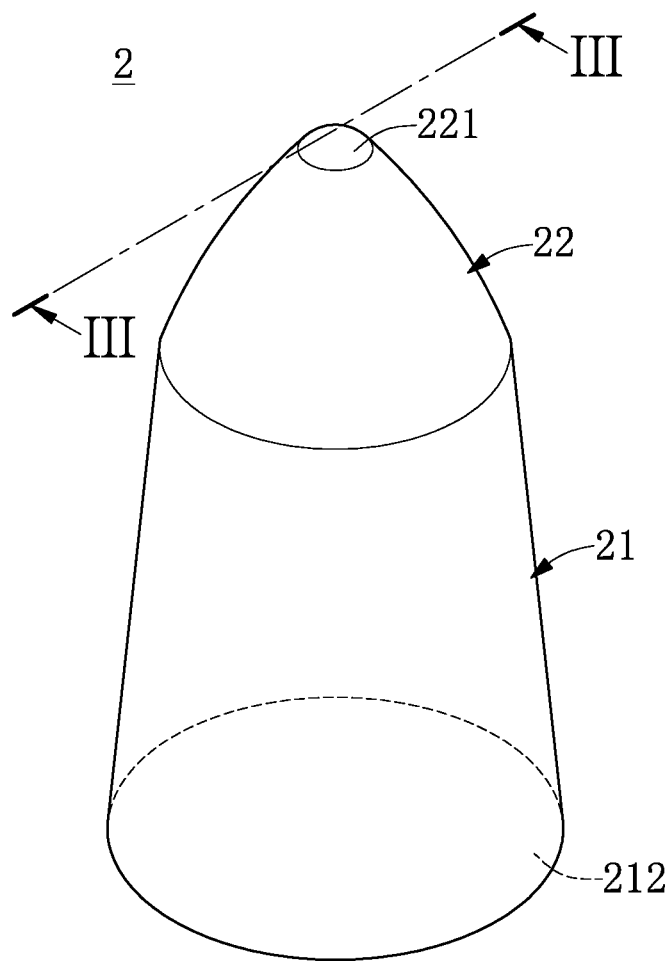
FIG. 2 is a perspective view of a biodegradable microneedle according to the first embodiment of the present disclosure.
Figure 3:
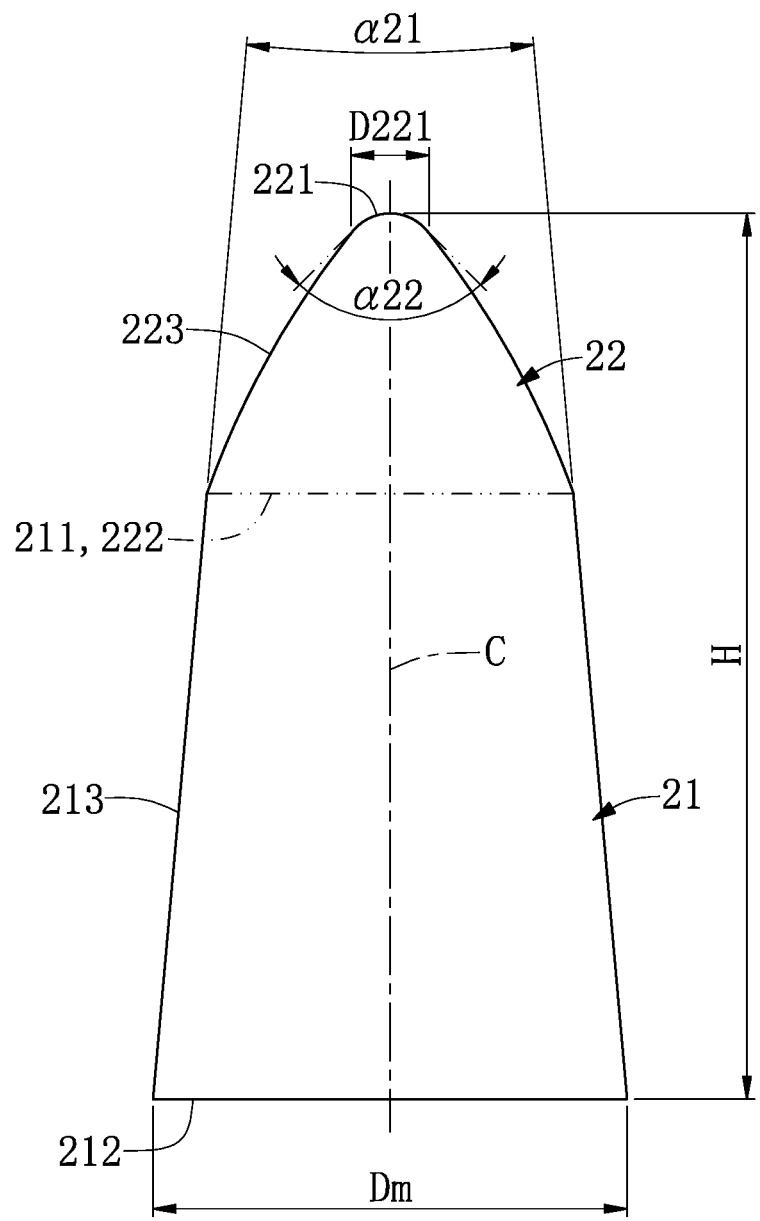
FIG. 3 is a cross-sectional view taken along line III-III of FIG. 2.

Referring to FIG. 1 to FIG. 3, a first embodiment of the present disclosure provides a microneedle structure 100. The microneedle structure 100 can be applied to human skin in a medical field or a cosmetic field. The microneedle structure 100 includes a base 1 and a plurality of biodegradable microneedles 2 disposed on the base 1.

Specifically, any microneedle not having biodegradable property is different from the biodegradable microneedle 2 of the present embodiment. Moreover, the biodegradable microneedle 2 in the present embodiment is used in cooperation with the base 1, but the biodegradable microneedle 2 in other embodiments of the present disclosure can be independently applied or can be used in cooperation with other components.

The base 1 in the present embodiment includes a flat carrying surface (not labeled) and is biodegradable, and the base 1 and the biodegradable microneedles 2 are integrally formed as a one piece structure, but the present disclosure is not limited thereto. For example, in other embodiments of the present disclosure, the carrying surface of the base 1 can be in a curved shape, or the base 1 can be provided without biodegradable property.

The biodegradable microneedles 2 in the present embodiment are formed on the base 1 by a matrix arrangement. As the biodegradable microneedles 2 are of the same structure or similar structure, the following description discloses the structure of just one of the biodegradable microneedles 2 for the sake of brevity, but the present disclosure is not limited thereto. For example, in other embodiments of the present disclosure, the biodegradable microneedles 2 of the microneedle structure 100 can be of different structure.

The biodegradable microneedle 2 in the present embodiment can be used to bring liquid for providing human skin to absorb, and can be degraded for providing human skin to absorb, but the present disclosure is not limited thereto. For example, in other embodiments of the present disclosure, the biodegradable microneedle 2 cannot be absorbed by human skin after being degraded.

For overall of the biodegradable microneedle 2, a longitudinal direction of the biodegradable microneedle 2 defines a central axis C, and the biodegradable microneedle 2 has a total height H along the central axis C and a maximum internal diameter Dm along a direction perpendicular the central axis C. The total height H of the biodegradable microneedle 2 in the present embodiment is within a range of 380-400 μm, and an aspect ratio defined by the total height H divided by the maximum internal diameter Dm is within a range of 1.6-2.25. The aspect ratio is preferable within a range of 1.8-2.0. In addition, any two of the biodegradable microneedles 2 of the microneedle structure 100 adjacent to each other respectively have two center points spaced apart from each other by a distance D that is preferably greater than or equal to the maximum internal diameter Dm, but the present disclosure is not limited thereto In other words, the biodegradable microneedle 2 in the present embodiment is a two-step structure different from structure of conventional microneedle, thereby effectively reinforcing the structural strength of the biodegradable microneedle 2. That is to say, any microneedle not formed as a two-step structure (e.g., a three-step structure) is different from the biodegradable microneedle 2 of the present embodiment.

Specifically, the biodegradable microneedle 2 includes a first step portion 21 connected to the base 1 and a second step 22 portion taperedly extending from the first step portion 21 along a direction away from the base 1 (e.g., an upward direction shown in FIG. 2). Moreover, a ratio defined by a height of the first step portion 21 in the total height H divided by a height of the second step portion 22 in the total height H is within a range of 1.8-2.6, so that the first step portion 21 can be formed to provide a stronger supporting force to the second step portion 22.

Moreover, the first step portion 21 is tapered along a direction away from the base 1 (e.g., an upward direction shown in FIG. 2), and a top surface 211 of the first step portion 21 is entirely overlapped with a bottom surface 222 of the second step portion 22. In other words, an annular lateral surface 213 of the first step portion 21 is connected to (or extends from) an annular lateral surface 223 of the second step portion 22, and the first step portion 21 and the second step portion 22 do not have any step there-between, so that a torque generated by forcing the second step portion 22 with respect to the first step portion 21 can be reduced to increase the structural strength of the biodegradable microneedle 2.

In the present embodiment, the first step portion 21 is a conical frustum, and the second step portion 22 is a cone. A bottom surface 212 of the conical frustum (i.e., the first step portion 21) is connected to the base 1, and the top surface 211 of the conical frustum (i.e., the first step portion 21) is entirely overlapped with the bottom surface 222 of the cone (i.e., the second step portion 22).

In a cross section of the biodegradable microneedle 2 having the central axis C (as shown in FIG. 3), a part (i.e., a contacting end 221 described in the following description) of the second step portion 22 arranged away from the first step portion 21 has a corner $\alpha 22$, and the corner $\alpha 22$ has an angle (i.e., an angle of the annular lateral surface 223 in the cross section) within a range of 65-100 degrees and faces toward the first step portion 21. Accordingly, the biodegradable microneedle 2 can have a stronger structural strength based on the design of the two-step structure (e.g., the aspect ratio), so that the angle of the corner of the second step portion 22 is not limited to the conventional limitations for being manufactured easily and being applied broader.

Specifically, in the cross section (as shown in FIG. 3), the annular lateral surface 213 of the first step portion 21 has an angle $\alpha 21$ defined by extending the annular lateral surface 213, and the angle $\alpha 21$ is within a range of 25-55 degrees and is less than the angle of the corner $\alpha 22$ of the second step portion 22. Accordingly, the first step portion 21 can be used to resist a larger torque and to provide a stronger supporting force to the second step portion 22 by being formed with the angle $\alpha 21$. In addition, the second step portion 22 includes a contacting end 221 arranged away from the first step portion 21, and the contacting end 221 has an arced surface having a diameter D221 within a range of 10-25 μm.

Second Embodiment

Figure 4:
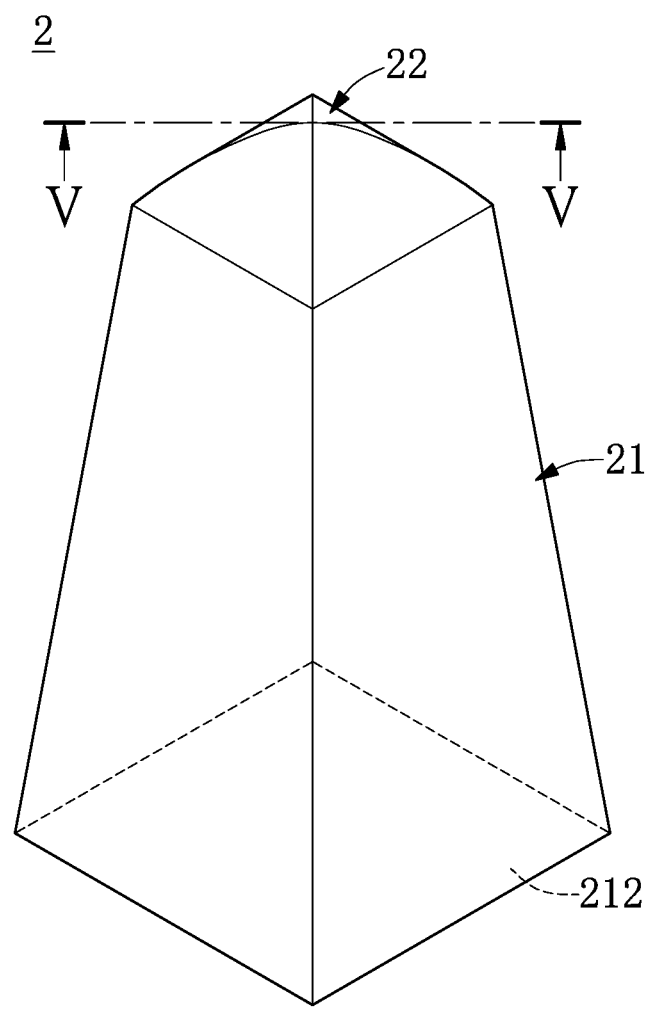
FIG. 4 is a perspective view of a biodegradable microneedle according to a second embodiment of the present disclosure.
Figure 5:
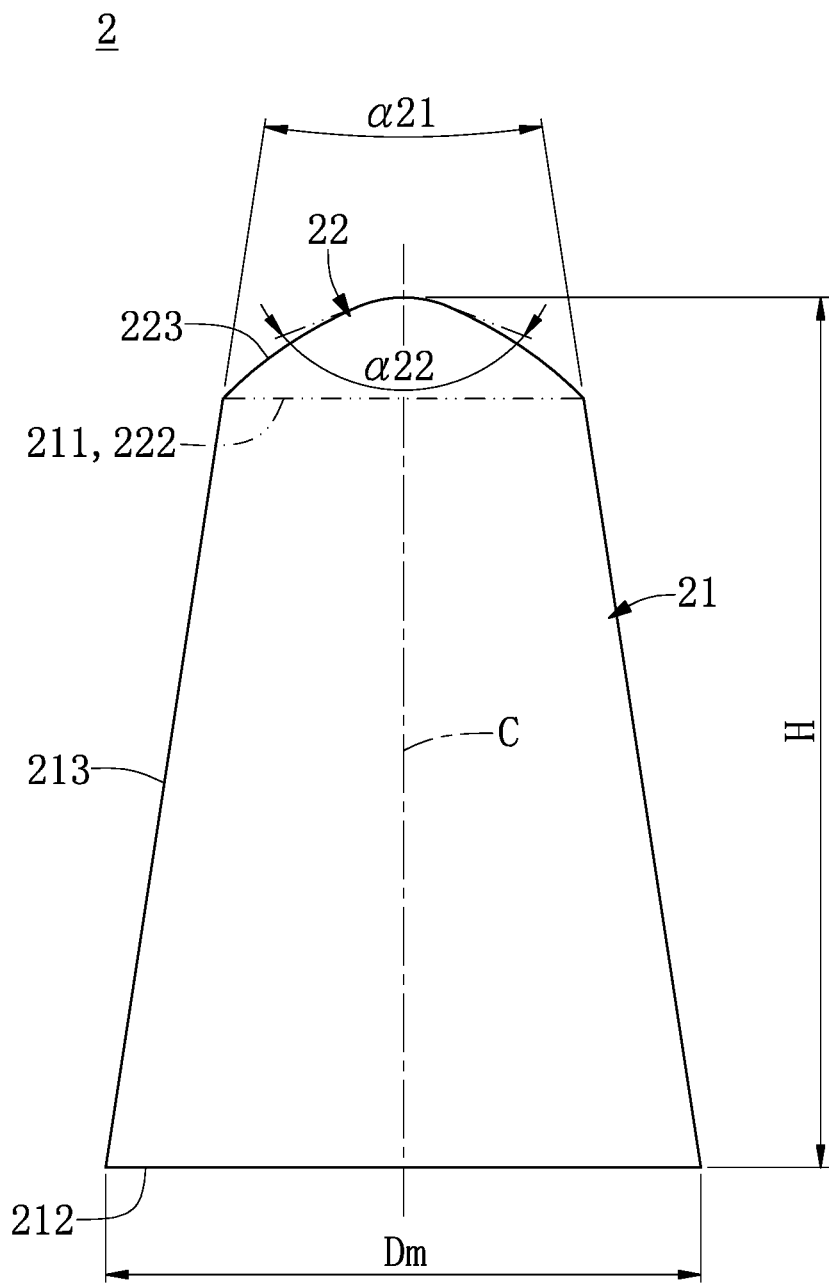
FIG. 5 is a cross-sectional view taken along line V-V of FIG. 4.

Referring to FIG. 4 and FIG. 5, a second embodiment of the present disclosure is similar to the first embodiment of the present disclosure. For the sake of brevity, descriptions of the same components in the first and second embodiments of the present disclosure will be omitted, and the following description only discloses different features (e.g., the biodegradable microneedle 2) between the first and second embodiments.

In the present embodiment, the total height H of the biodegradable microneedle 2 is within a range of 420-430 μm, and the aspect ratio defined by the total height H divided by the maximum internal diameter Dm can be within a range of 1.2-1.8. The aspect ratio is preferable within a range of 1.4-1.6. The ratio defined by the height of the first step portion 21 in the total height H divided by the height of the second step portion 22 in the total height H is within a range of 6.2-7.0.

Moreover, the first step portion 21 is a pyramidal frustum, and the second step portion 22 is a pyramid. The bottom surface 212 of the first step portion 21 is connected to the base 1, and the top surface 211 of the first step portion 21 is entirely overlapped with the bottom surface 222 of the second step portion 22.

Furthermore, in a cross section of the biodegradable microneedle 2 having the central axis C and the maximum internal diameter Dm (as shown in FIG. 5), a part of the second step portion 22 arranged away from the first step portion 21 has a corner $\alpha 22$ that has an angle within a range of 65-100 degrees and faces toward the first step portion 21, the annular lateral surface 213 of the first step portion 21 has an angle $\alpha 21$ defined by extending the annular lateral surface 213, and the angle $\alpha 21$ is within a range of 25-55 degrees and is less than the angle of the corner $\alpha 22$ of the second step portion 22.

Specifically, the first step portion 21 in the present embodiment is a quadrangular pyramidal frustum, the second step portion 22 is a quadrangular pyramid, but the present disclosure is not limited thereto. For example, in other embodiments of the present disclosure, the first step portion 21 can be a pyramidal frustum having N number of corners, the second step portion 22 can be a pyramid having N number of corners, and N is a positive integer more than two.

According to the description of the first and second embodiments, the total height H of the biodegradable microneedle 2 can be within a range of 380-430 μm, the aspect ratio defined by the total height H divided by the maximum internal diameter Dm can be within a range of 1.2-2.2, and the ratio defined by the height of the first step portion 21 in the total height H divided by the height of the second step portion 22 in the total height H is within a range of 1.8-7.0.

Third Embodiment

Figure 6:
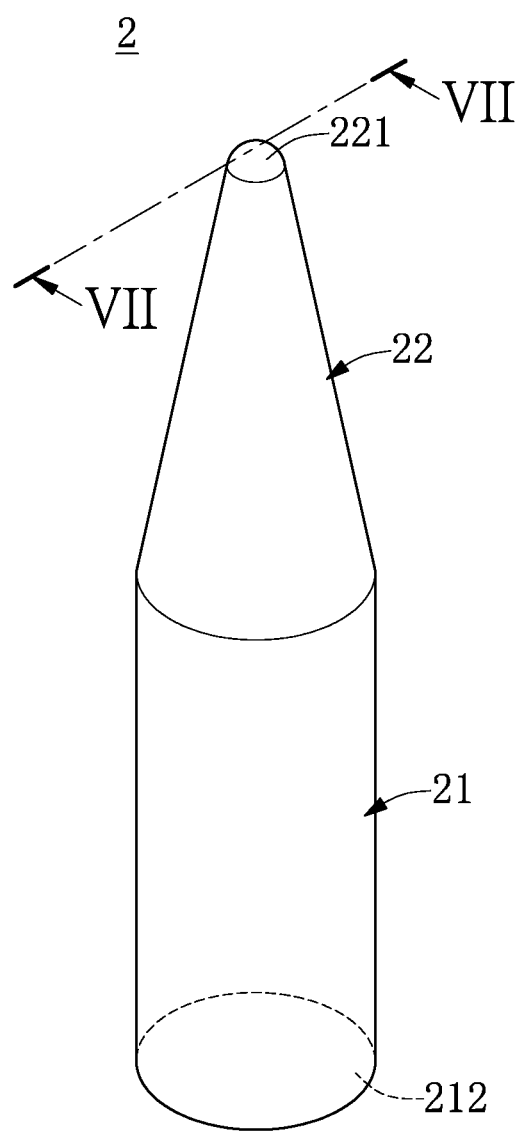
FIG. 6 is a perspective view of a biodegradable microneedle according to a third embodiment of the present disclosure.
Figure 7:
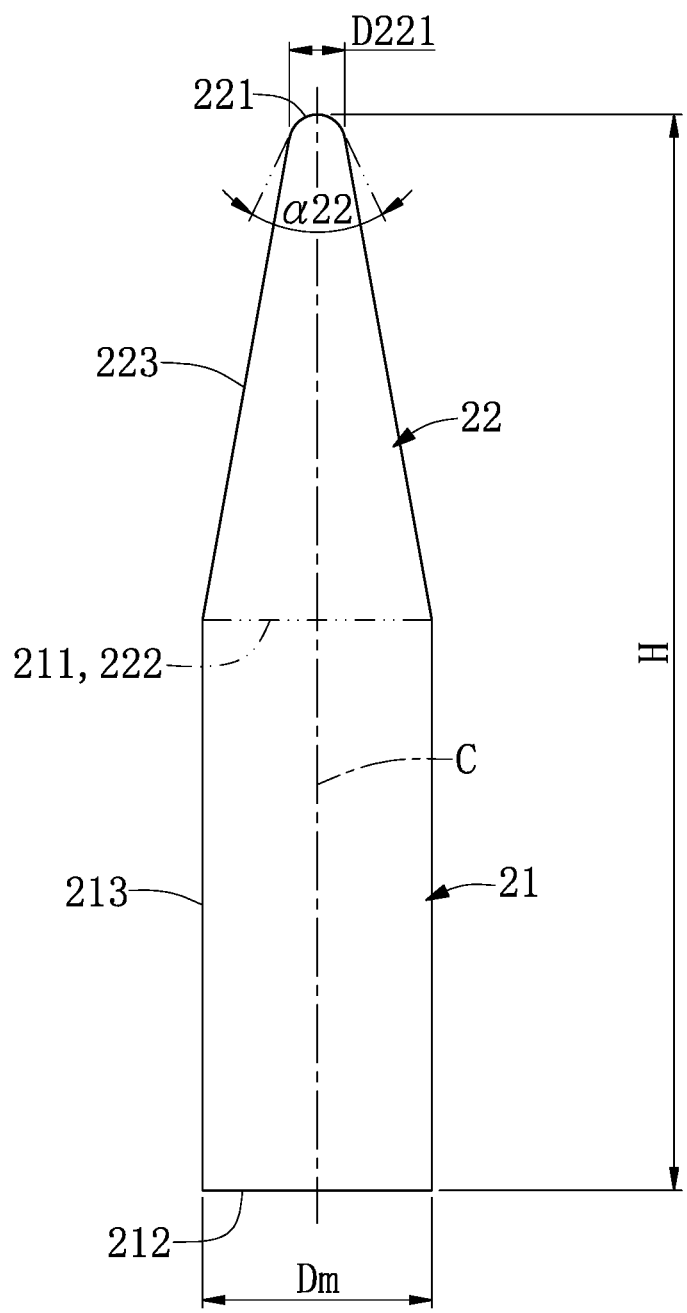
FIG. 7 is a cross-sectional view taken along line VII-VII of FIG. 6.

Referring to FIG. 6 and FIG. 7, a third embodiment of the present disclosure is similar to the first embodiment of the present disclosure. For the sake of brevity, descriptions of the same components in the first and third embodiments of the present disclosure will be omitted, and the following description only discloses different features (e.g., the biodegradable microneedle 2) between the first and third embodiments.

In the present embodiment, the total height H of the biodegradable microneedle 2 is within a range of 350-360 μm, and the aspect ratio defined by the total height H divided by the maximum internal diameter Dm is within a range of 4.5-5.0 (e.g., 4.7-4.9 is preferable), and the ratio defined by the height of the first step portion 21 in the total height H divided by the height of the second step portion 22 in the total height H is within a range of 1.9-1.1.

Moreover, any cross section of the first step portion 21 perpendicular to the central axis C are of the same shape and the same area. Specifically, the first step portion 21 is a cylinder, and the second step portion 22 is a cone. The bottom surface 212 of the first step portion 21 is connected to the base 1, and the top surface 211 of the first step portion 21 is entirely overlapped with the bottom surface 222 of the second step portion 22.

Furthermore, in a cross section of the biodegradable microneedle 2 having the central axis C (as shown in FIG. 7), a part of the second step portion 22 arranged away from the first step portion 21 has a corner $\alpha 22$ that has an angle within a range of 65-100 degrees and faces toward the first step portion 21. In addition, the contacting end 221 of the second step portion 22 has an arced surface having a diameter D221 less than 20 µm.

According to the description of the first to third embodiments, the total height H of the biodegradable microneedle 2 can be within a range of 350-430 µm, the aspect ratio defined by the total height H divided by the maximum internal diameter Dm can be within a range of 1.2-5.0, and the ratio defined by the height of the first step portion 21 in the total height H divided by the height of the second step portion 22 in the total height H is within a range of 0.9-7.0.

In conclusion, the biodegradable microneedle of the microneedle structure in the present disclosure is a two-step structure different from structure of conventional microneedle, thereby effectively reinforcing the structural strength of the biodegradable microneedle. Specifically, the biodegradable microneedle as disclosed in the first and second embodiments can have a stronger structural strength based on the design of the two-step structure (e.g., the aspect ratio), so that the angle of the corner of the second step portion is not limited to the conventional limitations for being manufactured easily and being applied broader.

In addition, the biodegradable microneedle as disclosed in the third embodiment is an elongated two-step structure (e.g., the aspect ratio is within a range of 4.5-5.0) for being provided to an application other than the first and second embodiments.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A microneedle structure, comprising:
a base; and
a plurality of biodegradable microneedles disposed on the base and each defining a central axis, wherein each of the biodegradable microneedles has a total height along the central axis and a maximum internal diameter along a direction perpendicular to the central axis, and wherein the total height is within a range of 380-430 µm, and an aspect ratio defined by the total height divided by the maximum internal diameter is within a range of 1.2-2.2,
wherein each of the biodegradable microneedles includes a first step portion connected to the base and a second step portion taperedly extending from the first step portion along a direction away from the base, wherein in a cross section of each of the biodegradable microneedles having the central axis, the second step portion has a contacting end for forming a microneedle tip, the contacting end is arranged away from the first step portion and has an angle within a range of 65-100 degrees, and the contacting end has an arced surface having a diameter within a range of 10-25 µm.

2. The microneedle structure according to claim 1, wherein in each of the biodegradable microneedles, the first step portion is tapered along a direction away from the base, and a top surface of the first step portion is entirely overlapped with a bottom surface of the second step portion.

3. The microneedle structure according to claim 1, wherein the base is biodegradable, and the base and the biodegradable microneedles are integrally formed as a one piece structure.

4. The microneedle structure according to claim 1, wherein the total height of each of the biodegradable microneedles is within a range of 380-400 µm.

5. The microneedle structure according to claim 1, wherein in each of the biodegradable microneedles, the first step portion is a pyramidal frustum, the second step portion is a pyramid, a bottom surface of the first step portion is connected to the base, and a top surface of the first step portion is entirely overlapped with a bottom surface of the second step portion.

6. The microneedle structure according to claim 5, wherein a ratio defined by a height of the first step portion in the total height divided by a height of the second step portion in the total height is within a range of 6.2-7.0.

7. The microneedle structure according to claim 1, wherein in each of the biodegradable microneedles, the first step portion is a conical frustum, the second step portion is a cone, a bottom surface of the first step portion is connected to the base, and a top surface of the first step portion is entirely overlapped with a bottom surface of the second step portion.

8. The microneedle structure according to claim 7, wherein a ratio defined by a height of the first step portion in the total height divided by a height of the second step portion in the total height is within a range of 1.8-2.6.

9. A biodegradable microneedle of a microneedle structure defining a central axis, comprising:
a first step portion; and
a second step portion taperedly extending from the first step portion along the central axis,
wherein the biodegradable microneedle has a total height along the central axis and a maximum internal diameter along a direction perpendicular to the central axis, wherein the total height is within a range of 380-430 µm, and an aspect ratio defined by the total height divided by the maximum internal diameter is within a range of 1.2-2.2, wherein in a cross section of the biodegradable microneedle having the central axis, the second step portion has a contacting end for forming a microneedle tip, the contacting end is arranged away from the first step portion and has an angle within a range of 65-100 degrees, and the contacting end has an arced surface having a diameter within a range of 10-25 µm.

10. A biodegradable microneedle of a microneedle structure defining a central axis, comprising:
a first step portion; and
a second step portion taperedly extending from the first step portion along the central axis,
wherein the biodegradable microneedle has a total height along the central axis and a maximum internal diameter along a direction perpendicular to the central axis, wherein the total height is within a range of 350-430 µm, and an aspect ratio defined by the total height divided by the maximum internal diameter is within a range of 1.2-5.0, wherein in a cross section of the biodegradable microneedle having the central axis, the second step portion has a contacting end for forming a microneedle tip, the contacting end is arranged away from the first step portion and has an angle within a range of 65-100 degrees.

* * * * *